United States Patent [19]

Shoher et al.

[11] Patent Number: 5,332,622
[45] Date of Patent: Jul. 26, 1994

[54] MOLDABLE DENTAL MATERIAL FOR FORMING OR REPAIRING A DENTAL RESTORATION

[76] Inventors: Itzhak Shoher, 50 Shlomo Hamelech St., Tel-Aviv, Israel, 64386; Aharon E. Whiteman, J.L. Peretz St. 13, Petach Tikvah, Israel, 49206

[21] Appl. No.: 5,595

[22] Filed: Jan. 19, 1993

[51] Int. Cl.$^5$ .............................. B32B 5/16
[52] U.S. Cl. ................... 428/323; 428/212; 428/304.4; 428/307.3; 428/328; 428/457; 428/613; 433/223; 433/228.1; 29/160.6; 75/955; 419/2
[58] Field of Search ............... 428/323, 304.4, 307.3, 428/317.9, 613, 212, 328, 457; 433/206, 222.1, 223, 228.1; 419/2; 75/252, 955; 29/160.6

[56] References Cited

U.S. PATENT DOCUMENTS

| | | | |
|---|---|---|---|
| Re. 33,371 | 10/1990 | Shoher et al. | 164/80 |
| 2,839,379 | 6/1958 | Erasmus | 428/613 |
| 3,502,466 | 3/1970 | Vickery | 29/160.6 |
| 3,623,541 | 11/1971 | Schmitz | 164/337 |
| 3,845,807 | 11/1974 | Koon | 164/255 |
| 4,426,404 | 1/1984 | Shoher et al. | 427/2 |
| 4,431,449 | 2/1984 | Dillon | 75/246 |
| 4,554,218 | 11/1985 | Gardner et al. | 428/567 |
| 4,742,861 | 5/1988 | Shoher et al. | 164/80 |
| 4,822,694 | 4/1989 | Randin et al. | 428/615 |
| 4,990,394 | 2/1991 | Shoher et al. | 428/212 |
| 4,997,699 | 3/1991 | Shoher et al. | 428/212 |
| 5,272,184 | 12/1993 | Shoher et al. | 523/118 |

OTHER PUBLICATIONS

Webster's II New Riverside University Dictionary, Houghton Mifflin Company (1984, 1988), p. 491.

*Primary Examiner*—Patrick J. Ryan
*Assistant Examiner*—Marie R. Macholl
*Attorney, Agent, or Firm*—E. Lieberstein

[57] ABSTRACT

A moldable dental composition for use in forming or repairing dental restorations composed of a mixture of high- and low-fusing temperature metal particles, finely divided carbonaceous particles, preferably of activated carbon, and a volatile binder in a concentration, such that upon heat treatment at a temperature below the melting temperature of the high-fusing temperature metal particles but sufficient to melt the low-fusing temperature metal particles and binder, a porous metal structure is formed having a capillary network of voids and a high void volume. The voids are filled using a filler material of metal or ceramic.

8 Claims, No Drawings

MOLDABLE DENTAL MATERIAL FOR FORMING OR REPAIRING A DENTAL RESTORATION

FIELD OF THE INVENTION

This invention relates to an improved moldable dental material composition for forming and/or repairing dental restorations.

BACKGROUND OF THE INVENTION

In crown and bridge prosthodontics, metal copings are conventionally used to provide the essential structural strength and rigidity necessary for a dental restoration to resist the forces of mastication. In a ceramic-to-metal dental restoration, the metal coping forms the understructure, over which is applied a fired-on coating of porcelain or acrylic. A coating of porcelain is used over the coping for aesthetics and to simulate natural teeth. To the dental patient, color and the overall appearance of the dental restoration are critical factors in the satisfaction of the restoration. Accordingly, the color of the metal coping is important and should enhance the aesthetics of the restoration. For a ceramic-to-metal dental restoration, the metal coping should provide strength and background color.

In a co-pending application of Applicants entitled *Moldable Dental Material and Method*, Ser. No. 887,245, filed May 19, 1992, (now U.S. Pat. No. 5,234,343) a dental material composition is taught which can be readily shaped or molded into any desired shape for repairing and/or forming a dental restoration, without any investment or casting of the metal. The composition of the material and method of application is taught in Applicants' U.S. Pat. Nos. 4,742,861 and 4,990,394, the disclosure of which is herein incorporated by reference. In general, the dental material is composed of high- and low-fusing temperature metal particles combined in a matrix with a volatile binder for forming a dental restoration directly on a refractory die or model of the tooth or teeth to be restored. The material is shaped on the die into a desired configuration and heat-treated at a temperature to melt, or substantially melt, the low-fusing temperature metal particles and to volatize the binder, resulting in a porous, sponge-like structure having the shape it was given prior to heat treatment. A low-melting temperature filler material, preferably of gold, is then melted into the sponge-like structure to form a solid metal coping, with a configuration identical to the configuration of the shaped material on the refractory die before heat treatment and without experiencing distortion and/or shrinkage.

The solidified metal should possess a desirable color, which is reproducible with high accuracy, for use in forming a dental restoration. Heretofore, the process was sensitive to temperature and the atmosphere in the furnace. Even minor variations in the temperature during the heat treatment procedures would permit some oxidation of the metals to occur, which could deleteriously affect its color, and even more seriously, could inhibit the penetration and flow of filler material into the porous sponge, which would affect the size of the solidified structure. In fact, even the type of furnace used or its condition was able to affect the ability to accurately control the temperature during the heat treatment procedures. Although sophisticated furnace temperature control equipment is commercially available, the implementation of such equipment is costly and would be unacceptable to the dental practitioner.

The sensitivity to temperature variation also limited the process to the fabrication within the furnace of one restoration at a time, unless even more elaborate temperature control measures were taken.

SUMMARY OF THE INVENTION

The moldable dental composition for forming or repairing a dental restoration of the present invention comprises a mixture of high-fusing temperature metal particles having a melting temperature above a preselected heat-treatment temperature; low-fusing temperature metal particles having a melting temperature equal to or below said preselected heat-treatment temperature; finely divided carbonaceous particles in a concentration above at least 0.005 wt. % of the dental material; and a volatile binder, such that upon heat treatment for the dental material at said preselected heat treatment temperature, a porous metal structure is formed having a capillary network of voids with a high-void volume.

DETAILED DESCRIPTION OF THE INVENTION

The dental material of the present invention is a moldable composition of metal particles formed from a mixture of metal particles of high- and low-fusing temperature metals and a volatile binder. Upon heat treatment, the binder vaporizes, leaving a porous sponge-like structure having a capillary network of multiple voids uniformly distributed throughout the structure, with a void volume preferably of at least thirty percent (30%).

The binder may be any suitable vehicle which will vaporize upon heat treatment, to facilitate the formation of a porous structure. The binder may be in liquid or solid form or a combination thereof, and may be composed of organic or inorganic components. A suitable liquid binder, such as ethylene or polyethylene glycol, may be used, although a solid binder of a wax or a combination of wax and other volatile components, which will vaporize at the heat treatment temperature without leaving a residue, is preferred. The preferred binder is composed substantially or entirely of wax, with the remainder, if any, of an organic or hydrocarbon compound to control the malleability of the dental material. The concentration of the binder is preferably high enough to assure a void volume of at least thirty percent (30%). When the concentration of binder is at least thirty percent (30%) by volume, the relationship between void volume and binder is substantially one-to-one.

In addition to the metal particles and binder, the dental material should preferably contain a small amount of carbonaceous particles of preferably activated carbon. Activated carbon is a well-known, porous, carbonaceous material formed by heat-treating carbon or subjecting it to reaction with gases, sometimes adding chemicals, for example, zinc chloride, during or after carbonization, in order to increase its porosity. Its high porosity results in a very high surface area of many orders of magnitude larger than its untreated surface area. Activated carbon has a large absorption capacity to different gases. The carbonaceous particles from which activated carbon is formed may be of any conventional carbon material, including carbon black, coke flour, calcined lamp black flour, and the like. Suitable amounts of the activated carbon particles in the dental material of the present invention are from five-thousands of one percent (0.005%) of the weight of the metal mixture, to about three percent (3%) of the weight of the metal mixture, with 0.05 wt. % to 0.5 wt. % being preferred. Finely divided particles smaller than 250 millimicrons in average diameter is preferred. The carbon particles act as a reducing agent during the heat treatment procedures and, substantially burn out upon exposure to air, leaving little or no residue. The increased surface area provided by activated carbon permits a smaller concentration to be used with much greater absorption capacity relative to unactivated carbon particles. The activated carbon also burns away much more readily at the temperature of heat treatment, leaving little, if any, residue.

In accordance with the present invention, a filler material is melted into the voids of the heat-treated porous structure to solidify the structure for forming the final coping of the dental restoration or the final restoration itself. The porous metal structure may be reshaped, if desired, into its final configuration before the filler material is added. The filler material may be any suitable ceramic or metal composition, preferably a precious metal composition. The filler material may also be formed of a matrix of particles mixed with a wax binder having a composition and concentration similar to the composition and concentration of the binder used to form the porous structure. A minimum binder concentration of at least about thirty percent (30%) by volume is preferred, and up to eighty-five percent (85%) by volume. At least fifty percent (50%) of the overall weight of the filler composition is preferably of individual or alloyed particles, of any size, containing between 90% to 98.5% gold and between 1.5% to 8.5% silver, preferably 2% to 5%, with the remainder selected from the group of metals such as copper, zinc, aluminum, magnesium, gallium, indium, tin, or any of the platinum group metals and/or elements from the third or fourth groups of elements of the periodic table. The weight of the remainder should not exceed seven percent (7%) of the total weight. The other fifty percent (50%) of the filler composition may be composed entirely of gold, although other metals may be included, provided the silver content of the total filter composition is limited to no more than ten percent (10%) by weight, and the total of the other metals is also limited to ten percent (10%) by weight. The addition of metals, other than gold and silver, may be added to provide a melting gradient during melting of the filler material.

If wax is used as the binder, its composition is not critical, and any natural wax, mineral wax, organic wax, or synthetic wax composition may be used. The preferred wax is relatively soft and tacky, and should melt relatively cleanly, as should any other binder constituent, without leaving a significant residue. The vaporizing temperature of the binder must be below the melting temperature of the low-fusing temperature metal particles, and below the melting temperature for the filler material. Moreover, the high- and low-fusing temperature metal particles should combine with the binder and activated carbon particles to form a mixture with a uniform distribution of metal particles in the binder. Alternatively, the binder can be heated and the particles added and mixed, to form a uniform distribution of metal particles. The binder may include additives to control the malleability of the composition, and as a substitute for wax. The additives may be selected from elastomers, gums, synthetic rubbers, polysaccharides, and any organic or hydrocarbon compound similar to wax, such as paraffin oil. The additives should have a desirable vaporizing temperature at or below the heat treatment temperature, and should not leave a residue upon heat treatment.

The high-fusing temperature metal component of the base mixture of high- and low-fusing temperature metal particles may be of a single metal or metal alloy, preferably of precious metals such as platinum and/or palladium, in any desired proportion relative to each other, with or without other constituents such as gold, silver, copper, magnesium, aluminum, zinc, gallium, indium, and other metals or elements from the third, fourth, or fifth group of elements of the periodic table. Gold may be added to the high-fusing temperature metal component to increase the affinity of the high-fusing temperature metal component to the low-fusing temperature metal component. However, to minimize shrinkage at the dental margin, it is preferable but not critical to the present invention that a predetermined proportion of the high-fusing metal component contain a relatively high concentration of platinum and palladium.

The particles of low-fusing temperature metal are composed preferably of gold or a gold alloy, with gold as the major constituent. The preference for gold as the major constituent of the low-fusing component is based on its known characteristics of workability, biocompatibility, non-oxidizing properties, and color. The particles of high- and low-fusing temperature metal should be selected with the high-fusing temperature component having an average size above one (1) micron and preferably between four (4) microns and eighty (80) microns. The average size of the low-fusing temperature metal particles should preferably be no greater than 40 microns. The volume relationship of the metals in the mixture should be in a range of from about twenty (20%) to eighty percent (80%) of the low-fusing component relative to the high-fusing component, and preferably from forty (40%) to sixty-five percent (65%). The composition of the selected metal particles for the high- and low-fusing components will determine the optimum volume ratio. The weight ratio will vary with the specific gravity of the selected materials. The high-fusing particle may have any shape, although an irregular flake-like shape is preferred.

The concentration of the volatile binder in the base mixture of high- and low-fusing temperature metal particles predominantly controls the void volume of the porous structure after heat treatment, as well as the uniformity of the capillary network formed between the voids which, in turn, controls the absorption and accommodation of the filler material in the porous structure. The heat treatment must eliminate the binder, preferably without leaving a residue, and cause the low-fusing particles to melt to form a stable porous metal structure with a thirty (30%) to eighty percent (80%) void volume and a uniformly distributed void matrix. The void volume will substantially correspond in percent to the percent concentration of binder before heat treatment, provided it is above the minimum concentration of thirty percent (30%). The activated carbon is believed to reduce any oxygen which may be present during heat treatment into carbon dioxide, and protects the hot sponge from oxidizing in the presence of oxygen upon cooling.

In accordance with the preferred embodiment of the present invention, the high- and low-fusing temperature metal particles are mixed with the carbon or activated carbon particles and binder to form a moldable base material. The base material may be compressed into a compacted strip or in any desired geometrical shape, having any thickness between twenty-five (25) microns and ten (10) millimicrons. The filler material may, likewise, be compacted into a strip or other geometry, for ease of application to the porous structure.

To form a coping from the base material, the base material is applied to the surface of a die by hand-molding, using pressure, with or without the use of an adhesive. A conventional adhesive may be used or an adhesive composed of a wax with a solvent and other adhesive agents, fluxes, etc. Hand-molding is done with the aid of a spatula or other hand instrument. The carving of the base metal-wax material into a preferred shape may be done on a model and then removed, or supported in any other fashion, for heat treatment. The heat treatment may be done in a furnace or under or over a flame. The usual heat treatment temperature range for the base material is between 800° C. and 1200° C. The heat treatment of the filler material may also be done in a furnace or using a flame at a temperature substantially equal to, below, or slightly above the first heat treatment temperature.

During the heat treatment, the binder burns out to form the spongy structure. Filler material, of metal or ceramic, is then added to the porous structure and heat treated to form a dense solid coping. Once the metal coping is formed, a conventional porcelain or acrylic veneer may be applied thereover to form a conventional ceramic-to-metal or acrylic-to-metal restoration.

What is claimed is:

1. A moldable dental composition for forming or repairing a dental restoration comprising: high fusing temperature metal particles having a melting temperature above the temperature at which said moldable dental composition is selected to be heat treated to form said dental restoration; low fusing temperature metal particles in a volume relationship relative to the high fusing temperature metal particles in said composition of between 20% to 80% and having a melting temperature equal to or below said heat treatment temperature; carbonaceous particles in a concentration above at least 0.005 wt % of the dental composition and a volatile binder, such that upon heat treatment of the dental composition at said heat treatment temperature, a porous metal structure is formed having a capillary network of voids with a high void volume of between thirty to eighty percent.

2. A moldable dental composition, as defined in claim 1, wherein said carbonaceous particles are particles of activated carbon.

3. A moldable dental composition, as defined in claim 2, wherein said carbonaceous particles are finely divided.

4. A moldable dental composition, as defined in claim 3, wherein said volatile binder comprises at least fifty percent (50%) wax by volume.

5. A moldable dental composition, as defined in claim 4, wherein the concentration of said particles of activated carbon is between 0.05 wt. % and 0.5 wt. % of the dental composition.

6. A moldable dental composition, as defined in claim 5, further comprising a second composition for densifying the porous metal structure formed upon heat treatment of said mixture of high- and low-fusing temperature metal particles, wherein said second composition comprises a filler material having a melting temperature below the melting temperature of said high-fusing temperature metal particles.

7. A moldable dental composition, as defined in claim 6, wherein said filler material comprises gold.

8. A moldable dental composition, as defined in claim 6, wherein said filler material comprises a ceramic.

* * * * *